US008541645B2

(12) United States Patent
Sil et al.

(10) Patent No.: US 8,541,645 B2
(45) Date of Patent: Sep. 24, 2013

(54) ANIMAL MODEL FOR CIGARETTE-SMOKE-INDUCED ATHEROSCLEROSIS AND RELATED METHODS (75) Inventors: Alok Kumar Sil, Kolkata (IN); Tanusree Ray, Kolkata (IN); Palash Chandra Maity, Kolkata (IN)

(73) Assignee: University of Calcutta, Kolkata (IN)

( * ) Notice: Subject to any disclaimer, the term of this patent is extended or adjusted under 35 U.S.C. 154(b) by 607 days.

(21) Appl. No.: 12/633,437

(22) Filed: Dec. 8, 2009

(65) Prior Publication Data

US 2011/0099645 A1 Apr. 28, 2011

(30) Foreign Application Priority Data

Oct. 22, 2009 (IN) .......................... 1268/KOL/2009

(51) Int. Cl.
*A01K 67/00* (2006.01)
*A01K 67/027* (2006.01)

(52) U.S. Cl.
USPC ....................... 800/9; 800/8; 800/14; 800/18

(58) Field of Classification Search
None
See application file for complete search history.

(56) References Cited

U.S. PATENT DOCUMENTS

| | | | |
|---|---|---|---|
| 7,125,897 B1 | 10/2006 | Elsley | |
| 7,556,927 B2 | 7/2009 | Witztum et al. | |
| 7,960,606 B2 * | 6/2011 | Raffai et al. | 800/9 |
| 2004/0121362 A1 | 6/2004 | Whitney | |
| 2004/0162329 A1 | 8/2004 | Lockwood et al. | |
| 2005/0143411 A1 | 6/2005 | Hirayama | |
| 2006/0135623 A1 | 6/2006 | Cutler | |
| 2007/0166698 A1 | 7/2007 | Potter | |
| 2008/0072338 A1 | 3/2008 | Mizutani et al. | |
| 2008/0233580 A1 | 9/2008 | Han et al. | |

OTHER PUBLICATIONS

Lough et al. Arch Pathol Lab Med 1978;102:377-80.*
Panda et al. Free Radical Biol Med 2000;29:115-24.*
Bernhard et al. The FASEB J 2003;17:2302-4.*
Leite et al. BMC Cardiovasc Disord 2009 Feb;29:9:7, pp. 1-9.*
von Holt et al. Atherosclerosis 2009;205:135-43.*
Yuan et al. BMC Cardiovascular Disorders 2007;7:1.*
J Pharmacol Sci 2009;110:354-61, Epub Jul. 1, 2009.*
Andrews, J.W., et al., "Studies on the vitamin C requirements of channel catfish (*Ictalurus punctatus*)" (1974) J. Nutr., 105:557-61.
Birney, E. et al., "Inability of bats to synthesise L-ascorb acid," (1976) Nature 260(5552):626-8.
Chatterjee, I., "Evolution and the Biosynthesis of Ascorbic Acid," Science, Dec. 1973; 182: 1271-1272.
Chaudhuri, C., et al., "L-Ascorbic Acid Synthesis in Birds: Phylogenetic Trend," Science, Apr. 1969; 164:435-436.
Gaca, M.D., et al. (2005) published in the Proc. of the 12th World Congress on Heart Disease, Vancouver, BC, Canada, pp. 85-88.
Grollman A., et al., "Enzymic synthesis of L-ascorbic acid in different animal species," Arch Biochem Biophys. Jul. 1957, 69:458-467.
Gupta, S., et al., "Synthesis of I-ascorbic acid from d-glucurono-1,4-lactone conjugates by different species of animals," International Journal of Biochemistry, vol. 4, Issue 21, 1973, pp. 309-314.
Howard, G., et al., "Cigarette Smoking and Progression of Atherosclerosis," JAMA, (1998) 279:119-124.
Jenness, R. et al., "Ascorbic acid and I-gulonolactone oxidase in lagomorphs," Comparative Biochemistry and Physiology Part B: Biochemistry and Molecular Biology, vol. 61, Issue 3, 1978, pp. 395-399.
Jenness, R. et al., "Variation of I-gulonolactone oxidase activity in placental mammals," Comparative Biochemistry and Physiology Part B: Biochemistry and Molecular Biology, vol. 67, Issue 2, 1980, pp. 195-204.
Nakajima, Y. et al., "Histochemical detection of I-gulonolactone: phenazine methosulfate oxidoreductase activity in several mammals with special reference to synthesis of vitamin C in primates," Histochem. J., vol. 18, No. 4, 1969, pp. 293-301.
National Research Council, "Guide for the care and use of laboratory animals," in Publication No. 85-23 (rev.) NIH, Bethesda, MD: 1985.
Schroeter, M.R. et al., "Cigarette Smoke Exposure Promotes Arterial Thrombosis and Vessel Remodeling after Vascular Injury in Apolipoprotein E-Deficient Mice," J Vasc Res 2008;45:480-492.
Yess, Ni. et al., "Biosynthesis of Ascorbic Acid in the Acouchi and Agouti," J. Nutr. 1967 92: 331-333.
International Search Report for PCT/IB2010/001334 mailed Oct. 11, 2010.
Ferrer, E., et al., "Effects of cigarette smoke on endothelial function of pulmonary arteries in the guinea pig," Respiratory Research 2009, vol. 10, No. 76.
Hutchison, S. J., et al., "Testosterone Worsens Endothelial Dysfunction Associated With Hypercholesterolemia and Environmental Tobacco Smoke Exposure in Male Rabbit Aorta," JACC vol. 29, No. 4, pp. 800-807 (Mar. 15, 1997).
Lehr, H., et al., "Vitamin C prevents cigarette smoke-induced leukocyte aggregation and adhesion to endothelium in vivo," Proc. Natl. Acad. Sci, U S A, vol. 91, pp. 7688-7692, Aug. 1994.
Penn, A., et al, "Butadiene inhalation accelerates arteriosclerotic plaque development in cockerels," Toxicology, vol. 113, Issues 1-3, Oct. 28, 1996, pp. 351-354.

(Continued)

*Primary Examiner* — Q. Janice Li
(74) *Attorney, Agent, or Firm* — Foley & Lardner LLP (57) ABSTRACT

Provided herein are non-human animal models and related methods useful for the identification, characterization, and analysis of the effects of environmental stimuli on the development and progression of pathological conditions. The environmental stimuli can include, but are not limited to, exposure to tobacco (e.g., cigarette, etc.) smoke. Exemplary pathological conditions include, but are not limited to, atherosclerosis, other cardiovascular disease (CVD), and the like. Also provided herein are non-human animal models and related methods useful for the identification, characterization, and analysis of pharmaceutical compounds, compositions, and/or formulations that can be used to prevent or treat a given pathological condition brought on by exposure to a given environmental condition.

14 Claims, 3 Drawing Sheets

(56) References Cited

OTHER PUBLICATIONS

Ray, T., et al., "Vitamin C prevents cigarette smoke induced atherosclerosis in guinea pig model," J. Atheroscler Thromb., vol. 17, No. 8, 2010, pp. 817-827.
Sun, Y.P., et al., Metoprolol does not attenuate atherosclerosis in lipid-fed rabbits exposed to environmental tobacco smoke, Circulation, 1994, vol. 89, pp. 2260-2265.
Banerjee S, et al., "Black tea prevents cigarette smoke-induced apoptosis and lung damage," Journal of Inflammation; 2007,4:3.
King CG. et al., "Effects of vitamin C intake upon the degree of tooth injury produced by diphtheria toxins," AM J Public Health. 1940; 30:1068-1072.
Kockx MM. et al., "Apoptosis in atherosclerosis: beneficial or detrimental," Cardovasc Res. 2000; 45:736-746.
Maity PC. et al. "Potentiation by cigarette smoke of macrophage function against Leishmania donovani infection," Inflamm. Res. 2009; 58:22-29.
Massberg S. et al. "A critical role of platelet adhesion in the initiation of atherosclerotic lesion formation," J. Exp. Med. 2002; 196:887-896.
Misra A. et al. "Black tea prevents cigarette smoke-induced oxidative damage of proteins in guinea pigs." J. Nutr. 2003; 133.2622-2628.
Niki E. Antioxidants and atherosclerosis. Biochem Soc Trans. 2004;32.156-159.
Prandoni P. et al. "An association between atherosclerosis and venous thrombosis," N Engl J Med. 2003; 348:1435-1441.
Schuler M. et al. "Mechanisms of p53-dependent apoptosis," Biochem Soc Trans. 2001; 29:684-688.
Singh U. et al. "Oxidative stress and atherosclerosis," Pathophysiology. 2006; 13:129-142.
Tsujimoto Y., "Role of Bcl-2 family proteins in apoptosis: apoptosomes or mitochondria?" Genes to Cells. 1998; 3:697-707.
Tuder RM. et al. "Cigarette smoke extract decreases the expression of vascular endothelial growth factor by cultured cells and triggers apoptosis of pulmonary endothelial cells," Chest. 2000; 117:241S-242S.
Wang J. et al. "Cigarette smoke activates caspase-3 to induce apoptosis of human umbilical venous endothelial cells," Mol Gent Metab, 2001; 72:82-88.
Yamaguchia Y. et al. "Oxidants in cigarette smoke extract modify low-density lipoprotein in the plasma and facilitate atherogenesis in the aorta of Watanabe heritable hyperlipidemic rabbits," Atherosclerosis. 2001; 56:109-117.
Maeda, K. et al., "Enhanced oxidative stress in neutrophils from hyperlipidemic guinea pig," Atherosclerosis, vol. 181, No. 1,pp. 87-92, 2005.
Yutaka Nakashima et al., "ApoE-Deficient Mice Develop Lesions of All Phases of Atherosclerosis Throughout Arterial Tree." Arteriosclerosis and Thrombosis, vol. 14, pp. 133-140.
Karen S. Meir et al., "Atherosclerosis in the Apolipoprotein E-Deficient Mouse: A Decade of Progress," Arterioscler Thromb Vasc Biol., vol. 24, 2004, pp. 1006-1014.
Andrew R. Bond et al., "The Fat-Fed Apolipoprotein E Knockout Mouse Brachiocephalic Artery in the Study of Atherosclerotic Plaque Rupture," Journal of Biomedicine and Biotechnology, 2011, pp. 1-10.
Maria Luz Fernandez, "Guinea Pigs as Models for Cholesterol and Lipoprotein Metabolism," The Journal of Nutrition, 2001, vol. 131, pp. 10-20.
Maria Luz Fernandez et al., "Guinea Pigs: A Suitable Animal Model to Study Lipoprotein Metabolism, Atherosclerosis and Inflammation," Nutrition & Metabolism, vol. 3, 2006, pp. 1-6.
Michael E. Rosenfeld et al., "Advanced Atherosclerotic Lesions in the Innominate Artery of the ApoE Knockout Mouse," Arterioscler Thromb Vasc Biol., vol. 20, 2000, pp. 2587-2592.
Tzong-Shyuan Lee et al., "The Role of Interleukin 12 in the Development of Atherosclerosis in ApoE-Deficient Mice," Arterioscler Thromb Vasc Biol., vol. 19, 1999, pp. 734-742.

\* cited by examiner

Fig. 3

ANIMAL MODEL FOR CIGARETTE-SMOKE-INDUCED ATHEROSCLEROSIS AND RELATED METHODS

CROSS REFERENCE TO RELATED APPLICATIONS

This application claims priority to Indian Patent Application Serial No. 1268/KOL/2009 filed Oct. 22, 2009, the contents of which are incorporated by reference herein in its entirety.

BACKGROUND

Certain animal models used to assess diseases and conditions associated with exposure to tobacco smoke have been described (see, e.g., U.S. Patent Pub. No. 2008/0072338; U.S. Patent Pub. No. 2008/0233580; Banerjee et al. (2007) *J. Inflamm.* (*Lond.*), 4:3, etc.).

The references included throughout the disclosure are incorporated by reference to the extent that the subject matter of the references is not inconsistent with the disclosure.

SUMMARY

The following summary is illustrative only and is not intended to be in any way limiting. In addition to the illustrative aspect, embodiments, and features described below and elsewhere, further aspects, embodiments, and features will become apparent by reference to the drawings and the accompanying detailed description.

Provided herein are methods of producing a non-human animal model of a human pathological condition, wherein the methods comprise: a) exposing the animal model to an inhaled environmental stimulus for a period time sufficient to induce the pathological condition in the animal model; and b) determining the extent of the pathological condition in the animal model. In such methods, the environmental stimulus can be cigarette smoke. Also in such methods, the pathological condition can be atherosclerosis, other cardiovascular disease (CVD), and the like, including any such pathological condition, other than emphysema or other obstructive pulmonary disease, induced by or caused by exposure to an environmental stimulus like tobacco (e.g., cigarette smoke, etc.).

In the methods described herein, the exposure to the environmental stimulus can be from about 1 day to about 4 weeks or more. Furthermore, the animal model used in the methods of the present application can be a rodent, for example, including, but not limited to, a guinea pig.

In the methods of the present application, the antioxidant levels in the animal model can be regulated. Such regulation can be accomplished by manipulating the diet of the animal model. For example, the antioxidant can be any known antioxidant, including, but not limited to, vitamin C.

Also, provided herein are methods of evaluating one or more pharmaceutical compounds, compositions, and/or formulations (e.g., drugs, etc.) useful for the prevention or treatment of a pathological condition, wherein the methods comprise: a) exposing a non-human animal model to an inhaled environmental stimulus for a period of time sufficient to induce the pathological condition in the animal model, wherein the animal model has further been exposed to one or more pharmaceutical compounds, compositions, and/or formulations either before the pathological condition has developed in the animal model or after the pathological condition has developed in the animal model; and b) determining whether the one or more pharmaceutical compounds, compositions, and/or formulations has prevented the development of the pathological condition in the animal model when the animal model was exposed to the one or more pharmaceutical compounds, compositions, and/or formulations before exposure to the environmental stimulus or whether the one or more pharmaceutical compounds, compositions, and/or formulations has ameliorated the symptoms of the pathological condition in the animal model when the animal model was exposed to the one or more pharmaceutical compounds, compositions, and/or formulations after or concurrent with exposure to the environmental condition and after or concurrent with development of the pathological condition.

In such methods, the environmental stimulus can be cigarette smoke. Also in such methods, the pathological condition can be atherosclerosis, other cardiovascular disease (CVD), and the like, including any such pathological condition, other than emphysema or other obstructive pulmonary disease, induced by or caused by exposure to an environmental stimulus like tobacco (e.g., cigarette smoke, etc.).

In the methods described herein, the exposure to the environmental stimulus can be from about 1 day to about 4 weeks or more. Furthermore, the animal model used in the methods of the present application can be a rodent, for example, including, but not limited to, a guinea pig.

In the methods of the present application, the antioxidant levels in the animal model can be regulated. Such regulation can be accomplished by manipulating the diet of the animal model. For example, the antioxidant can be any known antioxidant, including, but not limited to, vitamin C.

Provided herein are non-human animal models for the identification and characterization of pharmaceutical compounds useful for the prevention and treatment of atherosclerosis, other cardiovascular disease (CVD), and the like, wherein the atherosclerosis, other cardiovascular disease (CVD), and the like are induced by exposure of the animal to cigarette smoke and wherein the animal is a guinea pig.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Provided herein are animal models for cigarette-smoke-induced atherosclerosis. The results disclosed herein demonstrate the development of atherosclerosis in guinea pig aorta after exposing the animals to cigarette smoke for about 3-4 weeks. Such rapid development of atherosclerosis is possible, at least in part, by varying the vitamin C supplementation in the diet of the animals. Such an animal model provides a cost-effective method for obtaining a great deal of information on cigarette-smoke-induced atherosclerosis, including, but not limited to, the efficacy of drugs against the disease, in a short time-frame. The animal model can also be used to identify new targets for therapeutic intervention in atherosclerosis.

Atherosclerosis is a chronic inflammatory disease characterized by gradual thickening and hardening of arteries (see, e.g., Glass, C. K. & Witztum, J. L. (2001) *Cell*, vol. 104, pp. 503-516; Howard, G. et al. (1998) *JAMA*, vol. 279, no. 2, pp. 119-124; etc.). Atherosclerosis is caused by the slow build-up of plaque on the interior of arterial walls that leads of the reduction of the diameter of the arterial lumen, which restricts blood flow. This results in clinical conditions such as myocardial infarction (see, e.g., Glass, C. K. & Witztum, J. L. (2001) *Cell*, vol. 104, pp. 503-516; etc.), which is a leading cause of death world-wide. An underlying mechanism of atherosclerosis is attributed to endothelial dysfunction (see, e.g., Gaça, M. D. et al. (2005) published in the *Proc. of the 12th World Congress on Heart Disease*, Vancouver, BC, Canada, pp. 85-88; etc.), which is induced by oxidative stress originating from several risk factors. Endothelial dysfunction is followed by a series of pathological events such as infiltration of inflammatory cells, uptake of oxidized low density lipoprotein (ox-LDL) by macrophages, migration and proliferation of vascular smooth muscle cells (VSMC), formation of vascular lesions with a fibrous plaque, etc. At the final stages, the fibrous plaque ruptures, causing thrombosis (see, e.g., Glass, C. K. & Witztum, J. L. (2001) *Cell*, vol. 104, pp. 503-516; Schroeter, M. R. et al. (2008) *J. Vasc. Res.*, vol. 45, no. 6, pp. 480-492; etc.).

Epidemiological studies have shown that cigarette smoking is a major cause of atherosclerosis (see, e.g., Bernhard, D. (2003) *FASEB J.*, vol. 17, pp. 2302-2304; Howard, G. et al. (1998) *JAMA*, vol. 279, no. 2, pp. 119-124; etc.). The exact mechanism(s) by which cigarette smoke induces atherosclerosis is not fully understood. Cigarette smoke contains high concentrations of oxidants and free radicals, including, but not limited to, super oxide anions, nitrogen oxides, reactive aldehyde species, carbon monoxide, hydrogen peroxide, as well as nicotine (see, e.g., Pryor, W. A. (1997) *Environ. Health Perspect.*, vol. 105, pp. 875-882; etc.). These compounds are thought to be absorbed into the systemic circulation with varying efficiency. They can contribute to the endothelial damage, either directly by interacting with the endothelium, or indirectly by inducing the generation of reactive oxygen species in endothelial and inflammatory cells. Other studies have demonstrated that aqueous extracts of cigarette smoke oxidize low-density lipoprotein (LDL) into ox-LDL (see, e.g., Yamaguchi, Y. et al. (2001) *Atherosclerosis*, vol. 156, pp. 109-117; etc.) and activate platelets in vitro (see, e.g., Girdhar, G. et al. (2008) *Biomed. Eng.*, vol. 36, pp. 1142-1151; etc.). Such events are considered to be important in the pathogenesis of atherosclerosis (see, e.g., Huo, Y. et al. (2002) *Nat. Med.*, vol. 9, pp. 61-67; etc.).

The currently available data are obtained either from epidemiological studies or based on in vitro cell culture studies. Since many cell types and systemic influences contribute to the onset and progression of atherosclerosis, results obtained from cell culture studies can only provide limited information. Therefore, an animal model would be useful in order to better understand cigarette-smoke-mediated events that lead to atherosclerosis. Such an animal model would also provide a useful tool for screening and testing pharmaceutical compounds, compositions, and/or formulations (e.g., drugs, etc.) against cigarette-smoke-induced atherosclerosis.

Provided herein are non-human animal models and related methods for assessing, characterizing, and analyzing the effects of environmental stimuli on the initiation and progression of human pathological conditions. For example, provided herein are non-human animal models and related methods useful for studying cigarette-smoke-induced atherosclerosis. In particular, the development of atherosclerosis in guinea pig aorta after exposing the animals to tobacco (e.g., cigarette) smoke. Such exposure leads to the formation of atherosclerotic plaque in the aorta of guinea pigs.

Cigarette smoke is a major risk factor for developing atherosclerosis, a cardiovascular disease that can lead to heart attack. For better management of such a disease, an in-depth knowledge of the onset and progression of the disease is desirable, as is as a readily useful system for testing, identifying, characterizing, etc. (i.e., evaluating) the efficacy of available drugs that might be useful in preventing or treating the disease.

Since it is difficult to explore atherosclerosis in people, it is preferable to use an non-human animal model that mimics as closely as possible the biological response of people. At present there exists no known non-human animal model for cigarette-smoke-induced atherosclerosis. Disclosed and claimed herein is a non-human animal model that mimics cigarette-smoke-induced atherosclerosis in humans.

Previously, mice have been used as an animal model in order to investigate various diseases that affect people. However, for investigating the effects of cigarette smoke, a mouse animal model system suffers from at least one serious drawback. For example, unlike humans, mice can synthesize vitamin C, which is a potent anti-oxidant and able to neutralize, at least in part, the oxidative stress caused by cigarette smoke. Other anti-oxidants are known to those skilled in the art, including, but are not limited to, carotenoids and carotenoid analogs (see, e.g., U.S. Patent Pub. No. 2004/0162329; etc.) as well as geranyl geranyl actone (GGA) and related analogs (see, e.g., U.S. Patent Pub. No. 2006/0135623; etc.). Provided herein is a non-human animal model, the guinea pig, that cannot synthesize vitamin C, analogous to humans. This model system is useful in studying the effects of tobacco (e.g., cigarette) smoke in the development of atherosclerosis.

Unlike other experimental animal models, the guinea pig exhibits similarities with humans in certain physiological parameters, including, but not limited to, a cholesterol distribution pattern in plasma that plays an important role in developing diet-induced atherosclerosis (see, e.g., Fernandez, M. L. (2001) *J. Nutr.*, vol. 131, no. 1, pp. 10-20; Fernandez, M. L. & Volek, J. S. (2006) *Nutr. Metab.*, vol. 3, p. 17; etc.). Provided herein, therefore, is an investigation of the use of guinea pigs as a non-human animal model for cigarette-smoke-induced atherosclerosis.

Additionally, the length of time needed to investigate the effects, and potential treatments, of cigarette-smoke-induced atherosclerosis should be considered, as it is useful to study the initiation (i.e. onset, etc.), progression, and possible or probable therapeutic intervention(s) within a suitable timeframe. In this regard, it is also useful for an investigator to be able to manipulate the progression of the disease. Since the anti-oxidant properties of vitamin C can, at least in part, antagonize the effects of cigarette smoking, it is useful to employ a non-human animal model system that does not synthesize vitamin C. This trait can be exploited during investigation by manipulating the in vivo levels of vitamin C through nutritional supplement. This, in turn, allows investigators to manipulate (i.e., regulate, etc.) the progression of the disease. Such manipulation is not possible in other typical animal model systems (e.g., mice) that synthesize vitamin C de novo.

Vitamin C (L-ascorbic acid) is an essential nutrient for humans, certain primates, certain other mammalian species (e.g., guinea pigs, bats, etc.), certain species of birds, and certain fish (see, e.g., Jenness, R. et al. (1980) *Comp. Biochem. Physiol.* 67B:195-204; Jenness, R. et al. (1978) *Comp. Biochem. Physiol.* 61B:395-399; Birney, E. et al. (1976) *Nature,* 260(5552):626-8; Andrews, J. & Murai, T. (1975) *J. Nutr.,* 105(5):557-61; Chatterjee, I. (1973) *Science,* 182: 1271-1272; Gupta, S. et al. (1973) *Int. J. Biochem.* 4:309-314; Chaudhuri, C. & Chatterjee, I. (1969) *Science,* 164:435-436; Nakajima, Y. et al. (1969) *Histochem. J.* 18:293-301; Yess, N. & Hegsted, D. (1967) *J. Nutr.* 92:331-333; Grollman, A. & Lehninger, A. (1957) *Arch. Biochem. Biophys.* 69:458-467; etc.).

Exposing an animal to one or more inhaled environmental stimuli includes, but is not limited to, introducing into the lungs of an animal model one or more of tobacco smoke, cigarette smoke, cigar smoke, pipe smoke, clove cigarette smoke, flavored cigarette smoke, smoke from burning coal, industrial smoke, gaseous compounds, atmospheric compounds, airborne compounds, airborne contaminants, atmospheric pollutants, and the like.

Pathological conditions contemplated herein include any condition, other than emphysema or other obstructive pulmonary disease, caused by and/or exacerbated by exposure of the animal model to one or more inhaled environmental stimuli. Such pathological conditions include, but are not limited to, cardiovascular diseases (CVDs) (e.g., atherosclerosis, etc.).

The animal models and related methods described herein can be used to measure inhaled-environmental-stimuli-induced effect(s) to organs and tissues in the animal model other than lung tissue. For example and by way of illustration, the methods, tests, and assays described herein measure the effect(s) of one or more inhaled environmental stimuli on the aorta, or other arteries and/or veins, of an animal model. It is also contemplated that such methods, tests, and assays, as well as other methods, tests, and assays described herein, can be performed on other non-lung organs and tissues of the animal model to assess the effect(s) of one or more inhaled environmental stimuli on those non-lung organs and tissues.

A test compound as contemplated herein includes, but is not limited to, any compound that is being tested for its effect(s) on one or more pathological condition(s) brought on by or worsened by exposure to one or more inhaled environmental stimuli. Such compounds include, but are not limited to, pharmaceutical compounds (e.g., drugs, etc.), active pharmaceutical ingredients (APIs), nutraceutical compounds (e.g., nutritional supplements, etc.), homeopathic compounds, vitamins, minerals, and the like.

Determining the presence and/or extent of a pathological condition can be accomplished by any means known to persons skilled in the art. Such means include, but are not limited to, preparing and analyzing aortic sections, preparing and analyzing arterial sections, preparing and analyzing venous sections, characterizing and analyzing lipid levels and/or concentrations, characterizing and analyzing lipoprotein levels and/or concentrations (e.g., low density lipoprotein (LDL), high density lipoprotein (HDL), etc.), characterizing and analyzing blood homocysteine levels and/or concentrations, characterizing and analyzing apoptosis in the relevant tissue cells (e.g., aortic tissue, arterial tissue, venous tissue, etc.), assessing the pathological condition with radiological techniques (e.g., x-ray photography, MRI scans, CAT scans, FRET scans, etc.), and the like. These procedures, techniques, and tests can be used to determine whether the one or more test compounds has prevented and/or ameliorated the one or more pathological conditions brought on by and/or worsened by the one or more environmental stimuli.

For purposes of illustration, the procedure, technique, or test can be performed prior to exposing the animal model to the one or more environmental stimuli and prior to development of the one or more pathological conditions in order to determine a baseline or control value or values. Also, the procedure, technique, or test can be performed after exposing the animal model to the one or more environmental stimuli and prior to development of the one or more pathological conditions in order to determine the effect of the one or more environmental stimuli on the animal model. Further, the procedure, technique, or test can be performed after exposing the animal model to the one or more environmental stimuli and after development of the one or more pathological conditions in order to determine the effect of the one or more environmental stimuli and/or the extent of the one or more pathological conditions on the animal model. Additionally, the procedure, technique, or test can be performed on the animal model either before or after exposing the animal model to one or more test compounds, whether prior to, concurrent with, or after exposure of the animal model to the one or more environmental stimuli and whether prior to or after development of one or more pathological conditions, in order to determine whether the one or more test compounds has prevented and/or ameliorated the development of the one or more pathological conditions. Other permutations of these scenarios known to persons skilled in the art are also contemplated herein.

Example 1

Materials and Methods

Two to six, preferably three to four, month old male guinea pigs weighing between about 350 to about 450 grams (g) are used. All animals are maintained on a vitamin C-free diet for 7 days in order to minimize the in vivo levels of vitamin C in plasma and tissues. After 7 days of vitamin C deprivation, the guinea pigs are given a dietary supplementation of about 1 milligram (mg) of vitamin C per day (1 mg vitamin C/day) to prevent the onset of scurvy. (It is known that a dose of 0.8 mg vitamin C/day is sufficient to maintain guinea pigs without the development of scurvy.) Thereafter, the guinea pigs are subjected to cigarette smoke exposure (3 cigarettes per animal per day (3 cigarettes/animal/day) with 2 puffs per cigarette (2 puffs/cigarette)). Two puffs per cigarette indicate that the burning of a cigarette is divided into two halves. In each half, animals are exposed to cigarette smoke for a period of 1 minute (min.). There is an interval of 1 min. between these two halves. During this interval, animals are exposed to normal atmospheric air. Likewise, 3 puffs/cigarette would indicate that the burning of a cigarette is divided into three approximately equal parts with two intervals in between.

Exposure of the guinea pigs to tobacco (e.g., cigarette, etc.) smoke is carried out essentially as described by Banerjee, S. et al. (*J. Inflamm.,* 4:3 (2007). The animals are placed in a smoke chamber similar to a vacuum desiccator comprising at least one open tube at the top and at least one side tube fitted with a valve. The volume of the chamber can be about 5 liters. A cigarette, or other source of tobacco smoke, is connected to the open tube at the top of the chamber and lit. Smoke is pulled into the chamber by mild suction applied to the side tube of the chamber. Once each "puff" is introduced into the chamber, the vacuum is discontinued for the indicated exposure time (e.g., 1 min, etc.). Following this exposure time, normal atmospheric air is drawn into the chamber and the animal is exposed to normal atmospheric air for the indicated time. Subsequently, the second "puff" of tobacco (e.g., cigarette, etc.) smoke is introduced into the chamber as indicated above.

Figure 1:
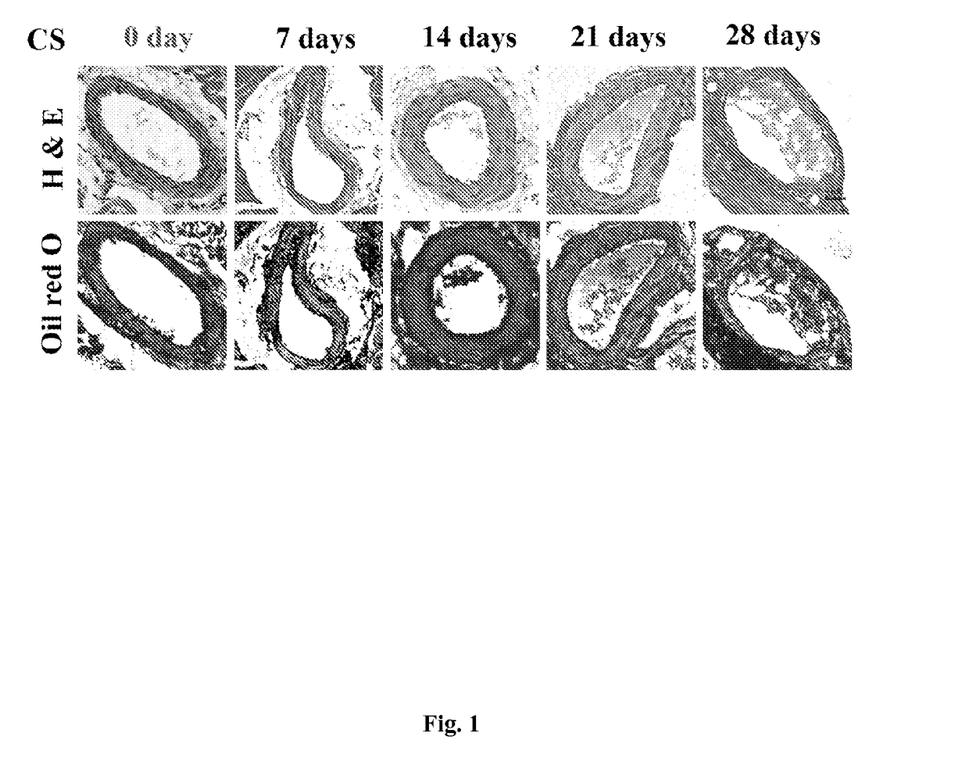
FIG. 1 provides an illustrative embodiment of atherosclerosis development in the animal model described herein.

This exposure is continued for different time periods (e.g., as shown in FIG. 1). Any commercially available cigarette can be used to generate the animal model disclosed and claimed herein. (For the data presented herein, a commercially available, filter-tipped cigarette (74 millimeters (mm), ITC brand, India) with a tar content of 15 mg and a nicotine content of 1 mg was used.) After exposure of the animals to the cigarette smoke, the animals are euthanized by standard methods known to those skilled in the art (e.g., diethyl ether inhalation, etc.). Thereafter, the aorta is removed from the animal and processed for further analysis. (All animal treatment procedures meet or exceed guidelines established by the U.S. National Institutes of Health (NIH) (i.e., "National research council guide for the care and use of laboratory animals." in Publication No. 85-23 (rev.) NIH, Bethesda, Md.:1985). As is known to those skilled in the art, other non-invasive and invasive methods of analysis can be used to determine the extent of the effects of the environmental condition on the initiation and/or progression of the pathological condition (see, e.g., U.S. Pat. No. 7,556,927; U.S. Pat. No. 7,125,897; U.S. Patent App. Pub. No. 2007/0166698; U.S. Patent App. Pub. 2005/0143411; U.S. Patent App. Pub. No. 2004/0121362; etc.). These methods of analysis can be used as well to determine the effects of a pharmaceutical compound, composition, and/or formulation on the prevention and/or treatment of a pathological condition caused by or induced by exposure to a given environmental condition.

The aorta obtained from the animal models that are exposed to cigarette smoke, or left unexposed (negative control), are fixed in 4% buffered formalin according to standard procedures. Formalin-fixed aortic tissue is embedded in paraffin and serially sectioned at 5 micrometer (μm) intervals, again according to standard procedures. The sections are stained with haematoxylin and eosin (H&E) as is known in the art. In order to determine the presence of lipid, adjacent sections are stained with oil red O and counterstained with haematoxylin, according to standard procedures. Likewise, quantitative assays for lipids are known in the art.

Results

In order to establish cigarette-smoke-induced atherosclerosis in guinea pigs, this animal model can be exposed to cigarette smoke for varying periods of time (see e.g., FIG. 1) and any changes that occur in the aorta, which is a primary site for atherosclerosis, can be assessed. This assessment can be done by H&E staining of formaldehyde-fixed paraffin sections obtained from aorta.

As shown in FIG. 1, when guinea pigs are exposed to cigarette smoke for 7 days (as described above in Materials and Methods), no change is observed when compared with the negative control. However, as the length of cigarette smoke exposure increases (e.g., about 14 days or more), the aorta shows clear symptoms and/or signs of atherosclerotic (e.g., atherogenic, etc.) changes. For example, at 14 days a visible intima-medial layer thickening is observed in some sections taken from the aorta. On or about 21 days and later, the endothelial layer is found to be broken at several locations and a massive network of complex plaque is observed within the aortal (aortic) lumen (see, e.g., FIG. 1). In contrast, no such structural alterations are observed in aortic sections taken from guinea pigs exposed only to air (see, e.g., FIG. 1). Moreover, certain aortal (aortic) lumen are found to be completely blocked by thrombus formation (see, e.g., FIG. 2). Oil red O staining of adjacent sections confirms the presence of high amounts of lipid within these thrombic structures, indicating a mature stage of atherosclerosis (see, e.g., FIGS. 1 and 2, bottom panels).

Figure 3:
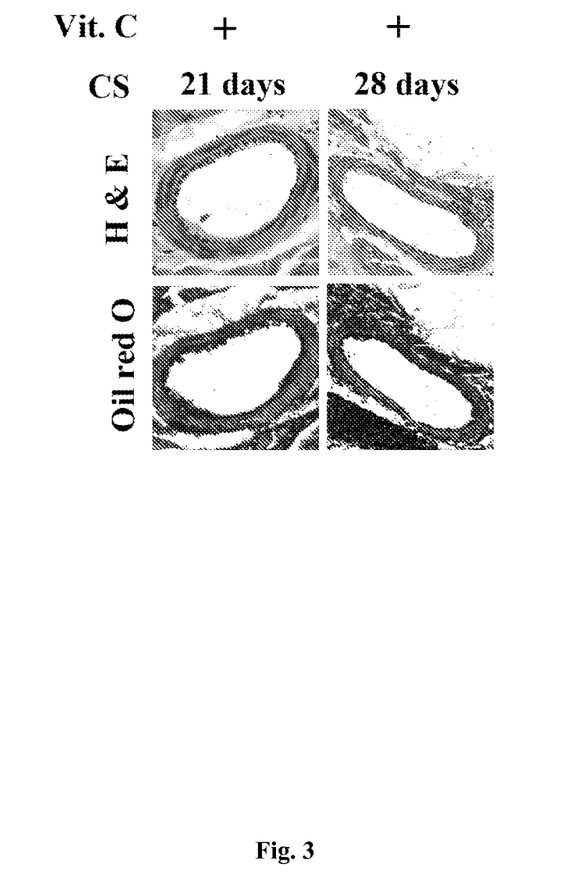
FIG. 3 provides an illustrative embodiment of an effect of vitamin C on atherosclerosis in the animal model described herein.

This animal model can be used to study the effects of numerous pharmaceutical compounds, compositions, and/or formulations (e.g., drugs, etc.) on the development and progression of a variety of pathological conditions, including, but not limited to, the effect of vitamin C on CS-induced atherosclerosis. FIG. 3 shows that dietary supplementation of vitamin C prevents CS-induced atherogenic changes in guinea pig aorta. Any drug or drug candidate that may or may not have an effect on CS-induced atherosclerosis can be similarly tested.

The data presented herein show that tobacco (e.g., cigarette, etc.) smoke exposure induces the development of atherosclerosis in a guinea pig animal model system.

FIG. 1 provides an illustrative embodiment of atherosclerosis development in the animal model described herein. FIG. 1 shows illustrative sections of guinea pig aortas following exposure of the guinea pigs to cigarette smoke (CS) for different periods of time (e.g., 0 (zero) days, 7 days, 14 days, 21, days, and 28 days). A minimum of 3 (three) animals are used for each time point. Aortas obtained from the guinea pigs are fixed in formaldehyde and paraffin sections were prepared. Thereafter, adjacent sections are stained with H&E (FIG. 1, top row) or Oil red O (FIG. 1, bottom row), as indicated.

Figure 2:
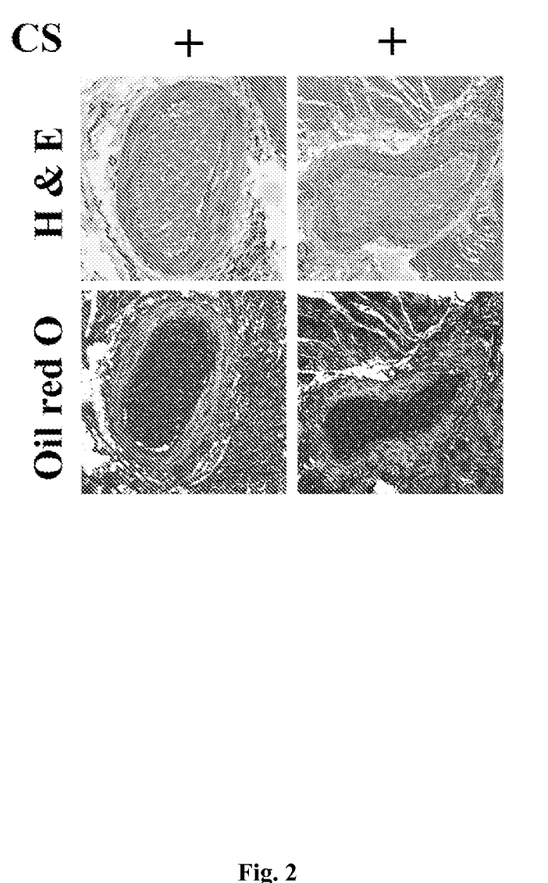
FIG. 2 provides an illustrative embodiment of thrombosis in the animal model described herein.

FIG. 2 provides an illustrative embodiment of thrombosis in the animal model described herein. FIG. 2 shows illustrative paraffin-embedded aortic sections obtained from guinea pigs exposed to CS for 4 weeks (CS+). Illustrative adjacent aortic sections are stained with H&E (FIG. 2, top row) or Oil red O (FIG. 2, bottom row), as indicated.

FIG. 3 provides an illustrative embodiment of an effect of vitamin C on atherosclerosis in the animal model described herein. Guinea pigs are fed with vitamin C (5 mg/day) supplemented food (Vit. C+) in addition to CS exposure. Illustrative adjacent paraffin embedded aortic sections are stained with H&E (FIG. 3, top row) or Oil red O (FIG. 3, bottom row), as indicated.

Discussion

As disclosed above, demonstrated herein is the development of a non-human animal model system for cigarette-smoke-induced atherosclerosis. Previously, guinea pigs have been shown to be an acceptable model system for diet-induced atherosclerosis. Unlike mouse model systems, guinea pigs exhibit a degree of similarity to humans in cholesterol distribution patterns (see, e.g., Fernandez, M. L. & McNamara, D. J. (1989) *Metabolism*, vol. 38, pp. 1094-1102; etc.). This attribute, at least in part, makes guinea pigs an acceptable animal model system for the investigation of high-cholesterol-diet-induced atherosclerosis (see, e.g., Fernandez, M. L. (2001) *J. Nutr.*, vol. 131, pp. 10-20; etc.).

In addition to the accumulation of cholesterol in the arteries, inflammatory responses also contribute to the development of atherosclerosis (see, e.g., Fernandez, M. L. et al. (2006) *Nutr. Metab.*, vol. 3, p. 17; etc.). An atherogenic inflammatory response has been demonstrated in a guinea pig animal model. (Id.). Like humans, guinea pigs cannot synthesize vitamin C, which is a known anti-oxidant, de novo (see, e.g., Sauberlich, H. E. (1994) *Ann. Rev. Nutr.*, vol. 14, pp. 371-391; etc.), thus dietary intake is the only source of this vitamin. For present purposes, the intake of vitamin C can be controlled, thereby minimizing its antagonistic effects on the oxidative stress caused by cigarette smoke exposure to biological systems in vivo.

As disclosed above, guinea pigs can be exposed to cigarette smoke for varying periods of time (e.g., about 0 days, about 7 days, about 14 days, about 21 days, about 28 days, or more, as well as any amount of time in between these discrete values). In order to account for variability and/or to gain statistical insights, the exposures can be run in triplicate. The data depicted in FIG. 1 demonstrate thickening of the aortic wall at some point between about 7 days and about 14 days, and clearly by about 14 days. At some point between about 14 days and about 21 days, and clearly by about 21 days, atherosclerotic plaques are observed in about 60% to about 70% of the aortic sections, as confirmed by oil red O staining. Similarly, a higher frequency of atherosclerotic plaques are observed after about 28 days as compared to the number of atherosclerotic plaques at about 21 days. At some point between about 21 days and about 28 days, and clearly by about 28 days, atherosclerotic plaques are observed in more than 80% of aortic sections. Additionally, in aortic sections of cigarette-smoke-exposed guinea pigs after about 28 days exposure, significant blockage of the aortic lumen is observed in particular tissue sections (see, e.g., FIG. 2).

It is noted that the guinea pig animal models begin dying prematurely after exposure to cigarette smoke for more than about 28 days. Due to the pleiotropic effects of cigarette smoke and its detrimental effects to normal physiology for a number of reasons, it is difficult to ascertain an exact cause of death for these animals. In light of the data disclosed herein, though, one of the contributing factors to the death of these animals can be the blockage of blood flow through the aorta due to cigarette-smoke-induced atherosclerotic symptoms, effects, and/or events.

Provided herein are useful non-human animal model systems, as well as related methods for generating and using these animal models, in the evaluation (e.g., identification, characterization, assessment, analysis, etc.) of preventative (i.e., prophylactic, etc.) and therapeutic pharmaceutical compounds, compositions, and/or formulations for the prevention and/or treatment of cigarette-smoke-induced (i.e., tobacco smoke) atherosclerosis.

Other methods and models are known for diagnosing, imaging, and assaying pathological conditions associated with exposure to harmful environmental stimuli, including, but not limited to, tobacco smoke and cigarette smoke (see, e.g., U.S. Pat. No. 7,556,927; U.S. Pat. No. 7,125,897; U.S. Patent Pub. No. 2007/0166698; U.S. Patent Pub. No. 2005/0143411; etc.). These other methods and models of diagnosing, imaging, and assaying are contemplated herein to be useful in conjunction with the non-human animal models and related methods provided herein.

The foregoing description of particular embodiments is presented for purposes of illustration and description only, and is not intended to be exhaustive or to limit the description to the precise form(s) disclosed. The description is selected to best explain the principles and practical application of the principles in order to enable others skilled in the art to best utilize the description. Various other embodiments and modifications as are suited to a particular use or purpose will be readily recognized by one skilled in the art.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, methods, and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method of producing a rodent model of atherosclerosis comprising the steps of:
    exposing the rodent model to an inhaled environmental stimulus for from about 14 days to up to 28 days; and
    analyzing the extent of atherosclerosis in the rodent model,
    wherein the environmental stimulus is cigarette smoke,
    wherein the rodent is a guinea pig, and
    wherein atherosclerosis is determined by aortic plaque formation, thickening of the aortic wall, and/or narrowing of the aortic lumen in rodents exposed to cigarette smoke as compared to rodents not exposed to cigarette smoke.

2. The method of claim 1 wherein antioxidant levels in the rodent model are regulated.

3. The method of claim 2 wherein the antioxidant levels are regulated by manipulating diet of the rodent model.

4. The method of claim 2 wherein the antioxidant is vitamin C.

5. A method of evaluating one or more test compounds useful for the prevention or treatment of atherosclerosis comprising the steps of:
    exposing a rodent model to an inhaled environmental-stimulus for from about 14 days to up to 28 days, wherein the rodent has further been exposed to one or more test compounds either before or after atherosclerosis has developed in the rodent; and
    analyzing whether the one or more test compounds have prevented the development of atherosclerosis in the rodent model when the rodent model was exposed to the one or more test compounds before exposure to the environmental stimulus or whether the one or more test compounds have ameliorated the symptoms of atherosclerosis in the rodent model when the rodent model was exposed to the one or more test compounds after or concurrent with exposure to the environmental stimulus and after or concurrent with development of atherosclerosis,
    wherein the environmental stimulus is cigarette smoke,
    wherein the rodent is a guinea pig, and
    wherein atherosclerosis is determined by aortic plaque formation, thickening of the aortic wall, and/or narrowing of the aortic lumen in rodents exposed to cigarette smoke as compared to rodents not exposed to cigarette smoke.

6. The method of claim 5 wherein antioxidant levels in the rodent model are regulated.

7. The method of claim 6 wherein the antioxidant levels are regulated by manipulating diet of the rodent model.

8. The method of claim 6 wherein the antioxidant is vitamin C.

9. A rodent model for the identification and characterization of test compounds useful for the prevention and treatment of atherosclerosis, wherein the atherosclerosis is induced by exposure of the rodent to cigarette smoke for from about 14 days to up to 28 days, wherein the rodent is a guinea pig, wherein atherosclerosis is determined by aortic plaque formation, thickening of the aortic wall, and/or narrowing of the aortic lumen in rodents exposed to cigarette smoke as compared to rodents not exposed to cigarette smoke.

10. The rodent model of claim 9, wherein antioxidant levels in the rodent are regulated by diet.

11. The rodent model of claim 10, wherein the antioxidant is vitamin C.

12. The rodent model of claim 9, wherein the rodent is not fed with high lipid or high cholesterol diet.

13. The method of claim 1, wherein the rodent model is not fed with high lipid or high cholesterol diet.

14. The method of claim 5, wherein the rodent model is not fed with high lipid or high cholesterol diet.

* * * * *